(12) United States Patent
Swann et al.

(10) Patent No.: US 8,434,490 B2
(45) Date of Patent: May 7, 2013

(54) DEVICES AND METHODS FOR OCCLUDING A FALLOPIAN TUBE

(75) Inventors: Betsy Swann, Grass Valley, CA (US); Christopher A. Stout, San Bruno, CA (US); Julian Cruzada, Sunnyvale, CA (US); Vidya Gopal, Germantown, MD (US); Charlotte Hermanto, Sunnyvale, CA (US)

(73) Assignee: Conceptus, Inc., Mountain View, CA (US)

( * ) Notice: Subject to any disclaimer, the term of this patent is extended or adjusted under 35 U.S.C. 154(b) by 0 days.

(21) Appl. No.: 13/195,773

(22) Filed: Aug. 1, 2011

(65) Prior Publication Data

US 2011/0284009 A1 Nov. 24, 2011

Related U.S. Application Data

(62) Division of application No. 12/110,145, filed on Apr. 25, 2008, now Pat. No. 7,987,853.

(51) Int. Cl.
*A61F 6/06* (2006.01)
*A61M 29/00* (2006.01)

(52) U.S. Cl.
USPC .......................................... 128/831; 606/193

(58) Field of Classification Search .......... 128/830–833, 128/838, 846, 887; 606/191, 192, 193, 197, 606/198, 200
See application file for complete search history.

(56) References Cited

U.S. PATENT DOCUMENTS

| | | | |
|---|---|---|---|
| 6,432,116 B1 * | 8/2002 | Callister et al. | 606/157 |
| 6,705,323 B1 * | 3/2004 | Nikolchev et al. | 128/830 |
| 8,062,325 B2 * | 11/2011 | Mitelberg et al. | 606/200 |
| 2002/0020417 A1 | 2/2002 | Nikolchev et al. | |
| 2005/0049666 A1 * | 3/2005 | Chien et al. | 623/1.11 |
| 2005/0192616 A1 * | 9/2005 | Callister et al. | 606/193 |
| 2008/0119943 A1 | 5/2008 | Armstrong et al. | |
| 2008/0125807 A1 * | 5/2008 | Wallace et al. | 606/200 |
| 2010/0082056 A1 | 4/2010 | Mavani et al. | |

\* cited by examiner

*Primary Examiner* — Michael Brown
*Assistant Examiner* — Ophelia A Hawthorne
(74) *Attorney, Agent, or Firm* — Blakely, Sokoloff, Taylor & Zafman LLP (57) ABSTRACT

Devices and method for occluding a fallopian tube. The devices, in one embodiment, may include a plurality of expandable occluding members coupled by respective dissolvable connecting members.

17 Claims, 7 Drawing Sheets

DEVICES AND METHODS FOR OCCLUDING A FALLOPIAN TUBE

RELATED APPLICATIONS

The present patent application is a divisional application of U.S. patent application Ser. No. 12/110,145, filed Apr. 25, 2008, entitled, "DEVICES AND METHODS FOR OCCLUDING A FALLOPIAN TUBE," now issued as U.S. Pat. No. 7,987,853, which is incorporated by reference.

BACKGROUND OF THE INVENTION

1). Field of the Invention

The present invention relates to devices and methods for occluding a fallopian tube to cause sterilization.

2). Discussion of Related Art

It is often desired or necessary for medical reasons to permanently close the fallopian tubes of women. The procedures currently proposed for occluding the fallopian tubes to effect sterilization include occlusion by insertion of a foreign body.

Fallopian tube occlusion by a foreign object presents many issues in creating an effectual design. The most important issue is preventing expulsion of the device by the fallopian tube. Fallopian tubes are functionally complex, and they have the ability to move objects through peristaltic (muscular contraction) and ciliated forces, and the direction of the force varies with menstrual cycle. In a recent study, a fallopian tube implant designed by American Medical Systems Holdings Inc. had an unacceptable number of expulsions. The device is believed to be overly rigid and thus had difficulty in placement and was ultimately ejected by the fallopian tube at a higher than acceptable rate. In order to achieve hysteroscopic tubal occlusion success, consistent delivery, acceptable placement location, and implant retention is critical. Such implants require a balance of flexibility, compressibility and rigidity. Flexibility is required to track the delivery system to the proper location, rigidity is required to either push the implant out of a delivery catheter or retract the delivery catheter while holding the implant in place and compressibility is required to retain the implant in the fallopian tube. Too much rigidity may be detrimental to long term success of the implant allowing the natural forces in the fallopian tube to either move the device into the peritoneal cavity or into the uterus.

SUMMARY OF THE SPECIFICATION

This invention provides in one embodiment a medical device for occluding a fallopian tube; the medical device includes an elongated member, a plurality of occlusion members removably coupled to the elongated member, and at least one dissolvable connecting member connected between at least two occlusion members. Each connecting member may also be removably coupled to the elongated member which can be used to deliver the entire medical device. Each connecting member may be electrolytically dissolvable. The medical device may additionally include fibers woven throughout the occlusion devices. The occlusion members may include radially expandable stents or stent-like structures. The occlusion members may include cylindrical coils. The occlusion members may include a mesh structure. The occlusion members may include spider members. The connecting members may be expandable. The occlusion or connecting member or both may include a shape memory polymer. The occlusion or connecting member may include a hydrogel. The occlusion or connecting member may include a closed cell foam.

The invention also provides in one embodiment a medical device for occluding a fallopian tube; the medical device includes an elongated member including an outer surface with a plurality of elongated circumferential indentations within the outer surface, and a plurality of expandable occlusion members, each respectively coupled within an indentation, wherein the outer surface of each of the expandable occlusion devices is even with the outer surface of the elongated member. The medical device may additionally include means for heating the plurality of occlusion devices coupled to the elongated member. The medical device may additionally include a mechanically expanding means for expanding the plurality of occlusion devices coupled to the elongated member. The medical device may additionally include fibers coupled to the plurality of expandable occlusion devices. The plurality of expandable occlusion members may be coupled to the elongated member by flexible fibers. The elongated member may float within the expandable occlusion members when the expandable occlusion members are expanded such that the elongated member does not transfer force between individual expandable occlusion members. The expandable occlusion devices may include cylindrical coils. The expandable occlusion devices may include a mesh structure. The expandable occlusion devices may include spider assemblies.

The invention also provides in one embodiment a method for occluding a fallopian tube, the method including inserting a distal portion of an elongated delivery member transcervically into a fallopian tube, the distal portion carrying a plurality of expandable occlusion members, delivering the plurality of expandable occlusion members into the fallopian tube, wherein the expandable occlusion members are coupled by a respective plurality of connecting members, expanding the plurality of expandable occlusion members inside the fallopian tube, and decoupling the plurality of connecting members from the plurality of expandable occlusion devices. Expanding the plurality of expandable occlusion members may include heating the expandable occlusion devices. Expanding the plurality of expandable occlusion devices may include mechanically expanding the expandable occlusion devices. The mechanical expansion may be a self expansion of each of the occlusion devices; for example, each of the occlusion devices may be formed from a shape memory material which is restrained in a delivery configuration and which expands from the restrained delivery configuration after it is released from the elongated delivery member. In certain embodiments, the mechanical expansion of the expandable occlusion device may be produced by the expansion of a balloon. Decoupling the plurality of connecting members may include passing a current to the plurality of connecting members. The current may electrolytically dissolve at least a portion of the connecting members. The expandable occlusion members may become decoupled from the elongated delivery member after expanding the plurality of expandable occlusion members. The expandable occlusion members may remain coupled, in other embodiments, to the elongated delivery member after expanding the plurality of expandable occlusion members.

BRIEF DESCRIPTION OF THE DRAWINGS

The invention is further described by way of example(s) with reference to the accompanying drawings, wherein.

DETAILED DESCRIPTION OF THE INVENTION

Figure 1A:
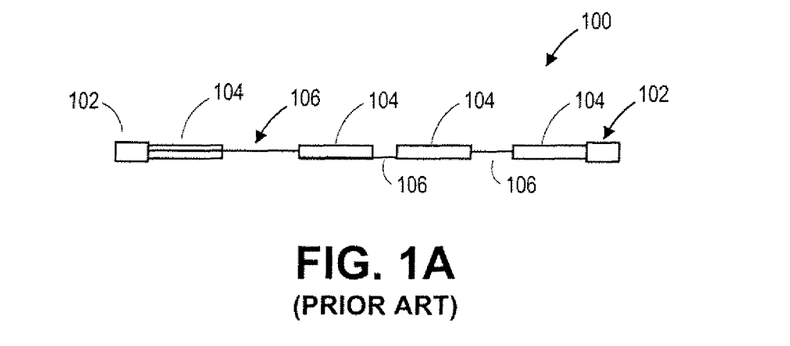
FIG. 1A is a side view of an unexpanded prior art tubal occlusion device.

FIG. 1A shows an example of a prior art fallopian tube implant 100 in a non-expanded configuration. The non-expanded configuration would be typically be implemented in a delivery device in a compact configuration. The implant 100 is characterized by a generally elongated body made up of several elements. The elements include two end portions 102, which have a radiopaque mass which is favorable to fluoroscopic viewing, and thus include materials such as gold, etc. The end portions 102 are included to make post-insertion (e.g. 3 months post-op) viewing possible. The implant 100 also includes expandable spider sections 104, shown non-expanded in FIG. 1A, and connecting members 106, which connect the expandable spider sections.

Figure 1B:
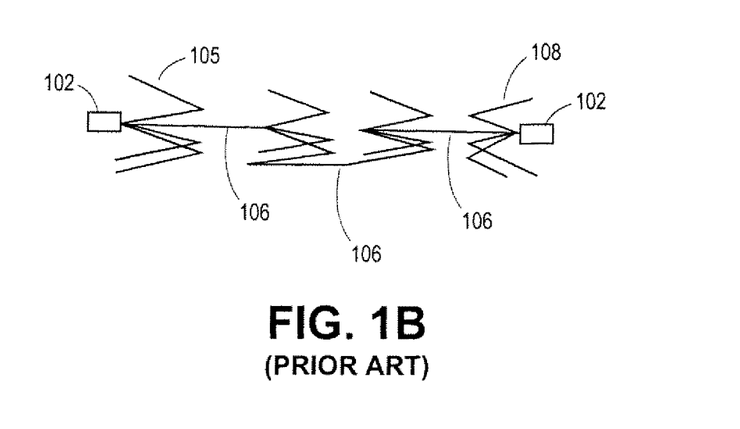
FIG. 1B is a side view of an expanded prior art tubal occlusion device.

FIG. 1B shows implant 100 in an expanded configuration, which is the configuration that typically exists after delivery in a fallopian tube. The spider sections 104 generally include at least two spider arms 108, but may include more for example three as shown. The spider arms 108 are generally made up of two members which are folded against each other in the non-expanded state. The spider sections 104 are connected by connecting members 106. More examples of spider sections and additional desirable elements are shown in co-assigned U.S. Published Patent Application No. US 20070227544 A1, which is hereby incorporated by reference in its entirety.

The connecting members 106 generally provide at least two roles; connecting individual spider sections 104 to provide relative stability in expansion and providing column strength to the implant 100 as a whole for pushing the device out of a catheter in order to deliver the implant. The connecting members 106 generally provide the stability and column strength needed for initial insertion and deployment into a fallopian tube. Typically the implant 100 is pushed out of the distal end of a catheter, and thus the implant must have sufficient column strength in order to prevent collapse and binding while pushing within the catheter. Also the fallopian tube is not round in cross-section and has a very complicated geometry; therefore an object inserted into the fallopian tube requires relatively high column strength in order to navigate the folds of the fallopian tube. However characteristics which are helpful for insertion and navigation of the fallopian tube may be detrimental for long term success of the implant 100, success being measured by successful permanent stabilization of the implant 100 in the fallopian tube.

Once expanded the individual spider sections 104 become engaged into the fallopian tube walls and are relatively stable within the fallopian tube, and thus have less need to be connected to other spider sections 104. The implant 100 is subjected to various forces which try to expel the implant 100. The fallopian tubes tend to exude objects through peristaltic (muscular contraction) and ciliated forces, and the direction of the force varies with menstrual cycle. Expulsion forces may not be universally applied throughout the fallopian tube; therefore different spider sections 104 undergo various individual expulsion forces. Thus the connecting members serve to transfer unwanted forces between the spider sections 104, after successful insertion and deployment into the fallopian tube.

Previously proposed devices simply suggest depositing a plurality of spider sections, which are not physically connected to one another, into the fallopian tube, in order to overcome the stiffness issues shown in FIGS. 1A-1B. This method is not practical in actual practice because ideally there needs to be some physical separation between devices in order to prevent unwanted interactions (e.g. transfer of expulsion forces) between the devices inside the fallopian tube which is not easily achievable and also the size of the devices makes it impracticable to effectively deposit them inside a fallopian tube because they lack enough stiffness in order to be effectively pushed out of a delivery catheter.

Figure 2A:
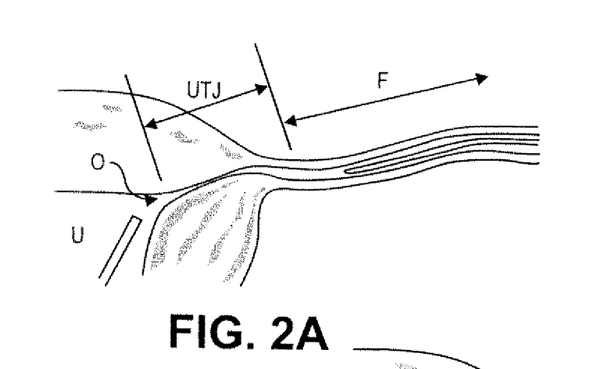
FIGS. 2A-2D show cross-sectional views of the delivery of a tubal occlusion device into a fallopian tube.

FIG. 2A shows a system and method of implanting a fallopian tube implant. The main fallopian tube F, the uterotubal junction UTJ, the uterus U, and the ostium O are shown in the cross sectional view of FIG. 2 A. The distal portion of a hysteroscope 200 is shown in a transcervical approach where the scope 200 enters the vagina and subsequently into the main section of the uterus U, and finally approaching the ostium O in preparation for delivery of an implant. The insertion of the scope may be performed in conjunction with fluoroscopy wherein a view similar to what is shown in FIG. 2A would be available to the operator of the system.

Figure 2B:
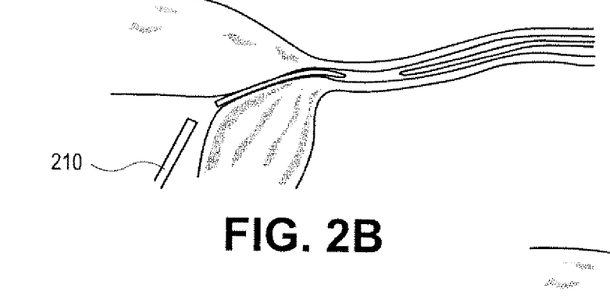

FIG. 2B shows the insertion of a catheter or elongated delivery member 210 into the UTJ. The catheter 210 is inserted into the UTJ once the ostium O is correctly identified, either visually via an hysteroscope or through fluoroscopy. The catheter is generally an elongated tubular member with an appropriate diameter for insertion into an hysteroscope and the ostium O, which is approximately 1 mm. It will also be preferable to have a tapered or rounded distal tip for easier insertion into the ostium O. A suitable marker on a portion of the catheter will visually (via the hysteroscope) or through fluoroscopy signify the correct depth of penetration of the catheter for deployment of the implant. Fallopian tube implants are typically designed to be deployed past the ostium or partially extending outside the ostium, of which this is the former.

Figure 2C:
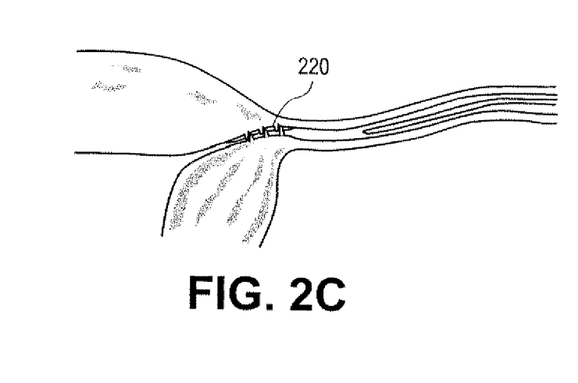

FIG. 2C shows the successful deployment of a fallopian tube implant 220. Fallopian tube tissue has grown into the implant and thus prevented entry of sperm or the release of an egg. The implant 220 is deposited past the ostium and would not be visible through an hysteroscopic inspection, but only visible through later fluoroscopy.

Figure 2D:
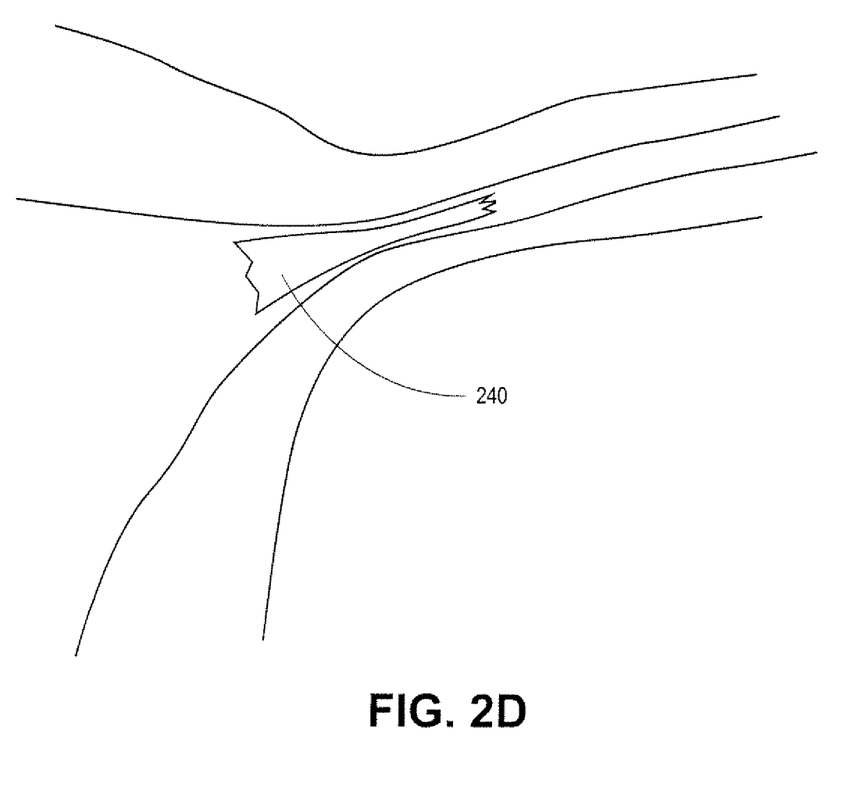

FIG. 2D shows the unsuccessful deployment of a fallopian tube implant 240. This type of implant is intended to be deployed past the ostium O, but is instead being forced out of the fallopian tube. This is called flowering of the implant 240, which is undesirable. The implant 240 will eventually be forced out of the UTJ resulting in a patent fallopian tube.

Figure 3A:
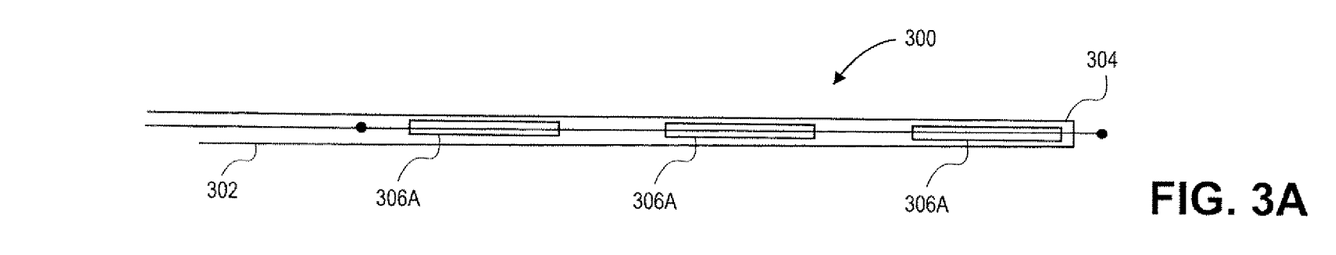
FIGS. 3A-3C show cross-sectional views of a device for tubal occlusion.

FIG. 3A shows one embodiment of the invention. A medical device 300 is shown which may include an elongated delivery member 302 and an expandable occlusion device 304. Typically, the device 300 will include a plurality of expandable occlusion members 306A which are shown in a collapsed configuration in FIG. 3A. These expandable occlusion members, after they expand, become the occlusion members 306 shown in FIG. 3B. The medical device 300 is shown in a compacted configuration at least partially disposed within the elongated delivery member 302, and also may be fully disposed within the elongated delivery member 302. The elongated delivery member 302 may be a catheter which includes a sheath which surrounds a lumen, and the expandable occlusion device 304 is held within the lumen during delivery (such as the delivery shown in FIG. 2B).

Figure 3B:
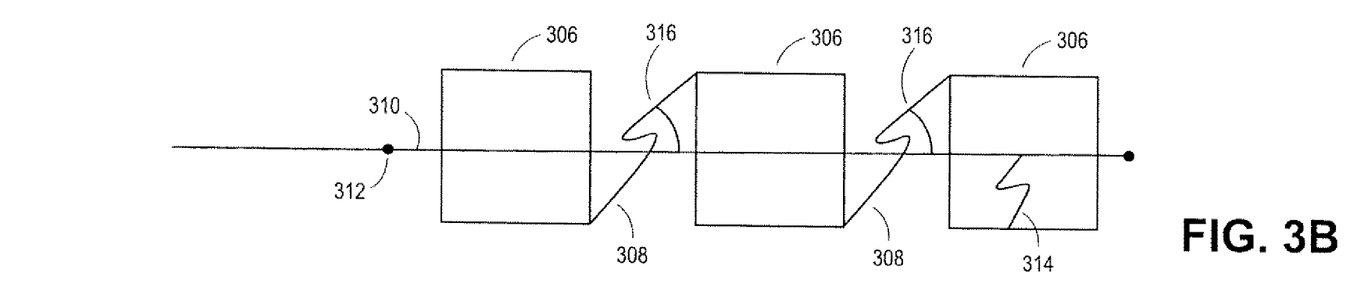

FIG. 3B shows the expandable occlusion device 304 in an expanded configuration. The expandable occlusion device 304 has been at least partially removed from the elongated delivery member 302. The expandable occlusion device 304 features a plurality of occlusion members 306 connected to each other by connecting members 308. The occlusion members 306 are shown in a generic form, but may take the form of radially expandable devices. The occlusion members 306 may take the form of expandable stents, coils, or spider devices. Generally the occlusion device 304 may be constructed from metal alloys (e.g. stainless steel), shape memory alloys, super-elastic alloys, polymers, biodegradable polymers, or biodegradable shape-memory polymers. Shape-memory polymers may be composed of two components with different thermal characteristics, such as oligo(ε-caprolactone)diol and crystallisable oligo(ρ-dioxanone)diol.

In the example shown the connecting members 308 are also expandable, but alternatively may keep a constant length under expansion. The connecting members 308 provide the occlusion device 304 column strength when pushing the device out of the elongated delivery member 302, as well as lateral flexibility for the distal portion of the medical device 300. Lateral flexibility is important because the tip of the device needs to bend in order to navigate the approach to the fallopian tube.

The connecting members 308 are coupled to an elongated center member 310. The center member 310 features an atraumatic tip as shown. The center member 310 also couples to at least a portion of the elongated delivery member 302 at joint 312. The center member 310 is designed to decouple from the elongated delivery member 302 at joint 312 for final delivery of the device into the fallopian tube. Joint 312 may be a mechanical joint, such as interference or threaded joint. The joint 312 may also be electrolytically dissolvable. The center member also serves to transfer force from the elongated delivery member 302 in order to push the expandable occlusion device 304 outside the elongated delivery member 302. The center member 310 may be connected to at least one occlusion member 306 via member 314, and also may be coupled to the connecting members 308 at dissolvable joints 316. The dissolvable joints 316 may also be electrically coupled to the center member and may be electrolytically dissolvable when a current is applied through the center member 302. Alternatively individual wire leads (not shown) may be attached to each dissolvable joint 316.

The center member 310 (or other parts of the occlusion device 304) may also carry fibers, such as polyester fibers, which encourage the growth of tissue into and around the implanted occlusion device 304. The fibers are not shown for clarity of the figure. Generally the fibers may be transversely located, with respect to the length of the center member (in addition to also being parallel with the length). The fibers may also be interwoven along the exterior of the expandable occlusion device 304.

Figure 3C:
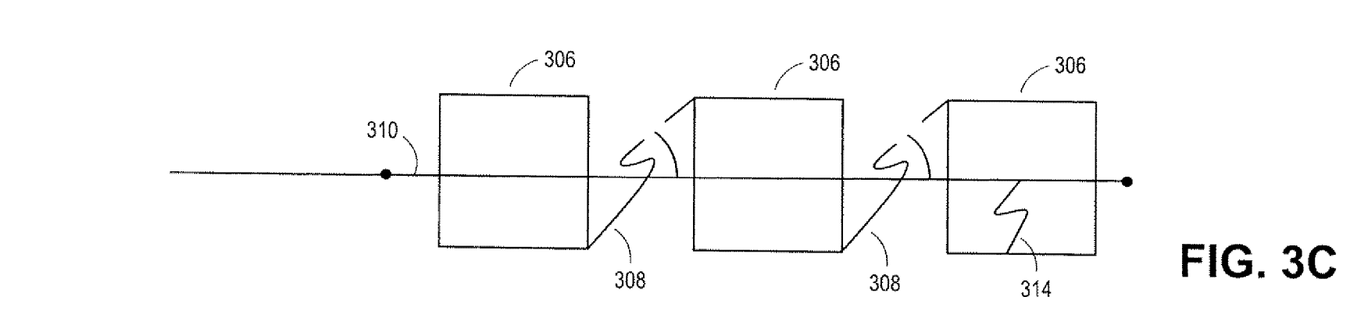

FIG. 3C shows the occlusion device 304 in an expanded and detached form. The device has been fully detached from the elongated delivery device 302 at joint 312. The dissolvable joints 316 have also been dissolved, which results in the occlusion members 306 being substantially independent from each other and the center member 310. In this embodiment, the only connection remaining, after dissolving the joints, between the center member 310 and the remainder of the device shown in FIG. 3C is the connection provided by member 314 (which connects the center member 310 to the distal most occlusion member 306). This configuration is advantageous because the occlusion device 304 uses the strength and flexibility of the connecting members prior to detachment and the occlusion members dissolve after detachment, therefore the occlusion members will not place expulsions forces against one another.

The center member 310 remains attached to at least one occlusion member 306 by member 314, and remains co-centrically positioned, or floating within the other occlusion members 306, and therefore does not transfer expulsion forces between occlusion members 306. The center member is desirable because it may carry fibers through the occlusion device 304. The center member 310 may still be coupled to the other occlusion members by fibers, which would not result in significant expulsion forces transferred between occlusion members 306. In an alternative embodiment the center member 310 would remain part of the elongated delivery device 302 after the joints 316 are dissolved, and not include member 314, and thus be withdrawn with the elongated delivery device 302.

Figure 4A:
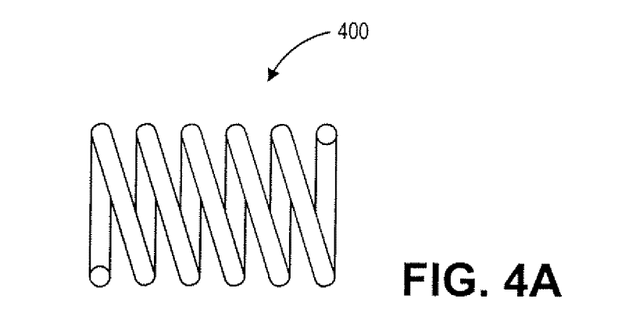
FIGS. 4A-4C shows side views of occlusion members.

FIG. 4A shows one embodiment of an occlusion member 306 as shown in FIGS. 3A-3C, and may be used for at least one of the occlusion members 306 shown in FIGS. 3A-3C. Occlusion member 400 is a coil shaped member. The member 400 is shown in an open configuration, whereby the coils have space between them. This is advantageous because the spacing between the coils allows tissue to grow into the inner region of the coil. Fibers may also be interwoven between and diametrically across the coils. Generally the occlusion member 400 may be constructed from metal alloys (e.g. stainless steel), shape memory alloys, super-elastic alloys, polymers, biodegradable polymers, or biodegradable shape-memory polymers. Shape-memory polymers may be composed of two components with different thermal characteristics, such as oligo(ε-caprolactone)diol and crystallisable oligo(ρ-dioxanone)diol. The coil may be reduced in diameter, before delivery, by winding the coil. The wound coil will thus have potential energy which is released to expand the coil into the shape as shown.

Figure 4B:
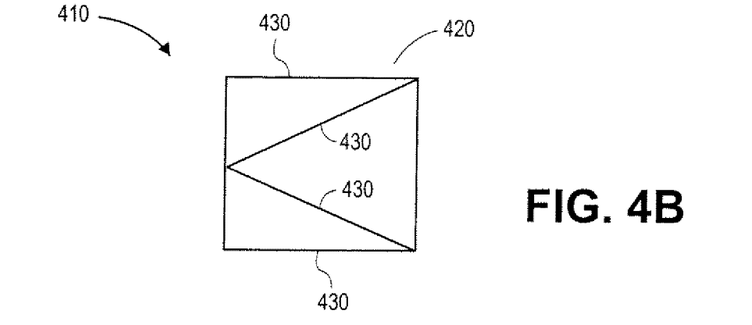

FIG. 4B shows one embodiment of an occlusion member 306 as shown in FIGS. 3A-3C, and may be used for at least one of the occlusion members 306 shown in FIGS. 3A-3C. FIG. 4B is a spider member 410. More examples of spider members which also may be used are shown in co-assigned U.S. Published Patent Application No. US 20070227544 A1, which was previously incorporated by reference. Each spider member 410 may include at least two spider arms 420. The spider arms 420 are generally made up of two members that are folded against each other in a non-expanded state (not shown). Fibers may also be interwoven between and diametrically across the spider arms 420. Generally the spider member 410 may be constructed from metal alloys (e.g. stainless steel), shape memory alloys, super-elastic alloys, polymers, biodegradable polymers, or biodegradable shape-memory polymers. Shape-memory polymers may be composed of two components with different thermal characteristics.

Figure 4C:
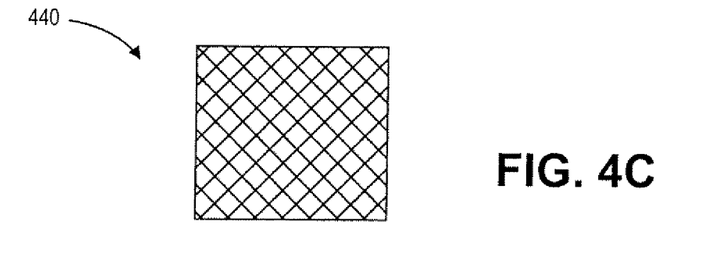

FIG. 4C shows one embodiment of an occlusion member 306 as shown in FIGS. 3A-3C, and may be used for at least one of the occlusion members 306 shown in FIGS. 3A-3C. FIG. 4C is a stent member 440. The stent member 440 may have a mesh configuration as shown. The stent member may be formed form interwoven wires, or alternatively formed (e.g. laser cut or chemically etched) from tubing. The stent member 440 will have an unexpanded state (not shown) wherein the stent member 440 will assume a smaller diameter, and may or may not have a longer length in the unexpanded state. Fibers may also be interwoven between and diametrically across the stent member 440. Generally the stent member 440 may be constructed from metal alloys (e.g. stainless steel), shape memory alloys, super-elastic alloys, polymers, biodegradable polymers, or biodegradable shape-memory polymers. Shape-memory polymers may be composed of two components with different thermal characteristics.

Figure 5A:
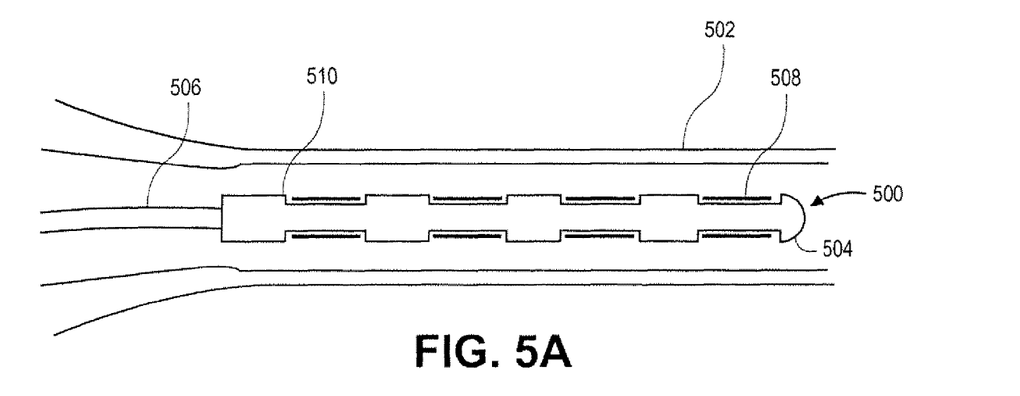
FIGS. 5A-5B show cross-sectional views of a device for tubal occlusion.
Figure 5B:
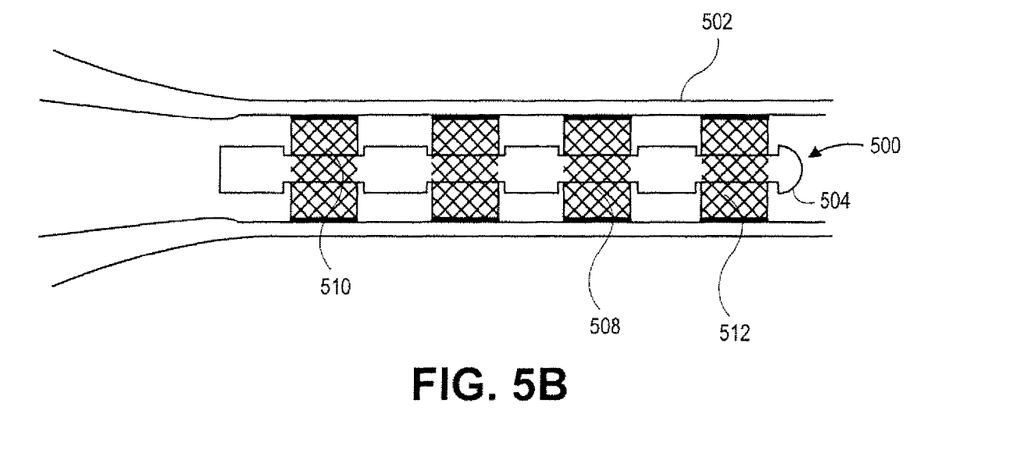

FIGS. 5A-5B shows another embodiment of the invention. Occlusion device 500 is shown as positioned within fallopian tube 502. The occlusion device 500 includes an elongated center member 504 coupled to at least a portion of an elongated delivery device 506. The occlusion device 500 also includes at least one, or a plurality of expandable occlusion members 508 detachably coupled to the center member 504. The occlusion members 508 may take the form as shown in FIGS. 4A-4C.

The center member may feature a plurality of elongated circumferential indentations 510 for the unexpanded occlusion members 508 to couple to. The elongated circumferential indentations 510 allow the outer surface of the distal portion of the occlusion device to be even with the outer surfaces of the unexpanded occlusion members 508 so as to prevent snagging of edges while feeding the occlusion device 500 through a scope or the fallopian tube. Edges are shown in the figure for clarity in distinguishing the elements.

Additionally heating elements may be coupled to portions of the elongated circumferential indentations 510 to expand occlusion members 508 constructed from shape-memory alloy. The elongated circumferential indentations 510 may also include mechanical elements to expand occlusion members 508, such as expansion balloons for occlusion members 508 constructed from malleable materials or moveable release wires to release occlusion members 508 which store potential energy (e.g. wound coil or super-elastic alloy) in an unexpanded state.

As shown the occlusion members 508 have been positioned within the fallopian tube prior to decoupling the occlusion devices from the center member 504. Generally the center member 508 may be constructed from metal alloys (e.g. stainless steel), shape memory alloys, super-elastic alloys, polymers, biodegradable polymers, or biodegradable shape-memory polymers. Shape-memory polymers may be composed of two components with different thermal characteristics.

FIG. 5B shows the occlusion device 500 expanded within the fallopian tube 502 and detached from the elongated delivery device 506. The elongated delivery device 506 may decouple from the occlusion device 500 by a mechanical joint (e.g. an interference or threaded joint), the joint may also be electrolytically dissolvable. The occlusion members 508 are expanded and fully engaged into the walls of the fallopian tube 502. The occlusion members 508 may remain coupled to the center member 504 by fibers 512. Thus the center member 504 floats within the centers of the occlusion members 508. This is advantageous because the center member serves to deliver the occlusion members 508, and then also provides a substrate for tissue growth. The center member 504 also does not transfer expulsion forces between individual occlusion members 508 because of the floating nature of the coupling between the occlusion members 508 and the center member 504.

Figure 6:
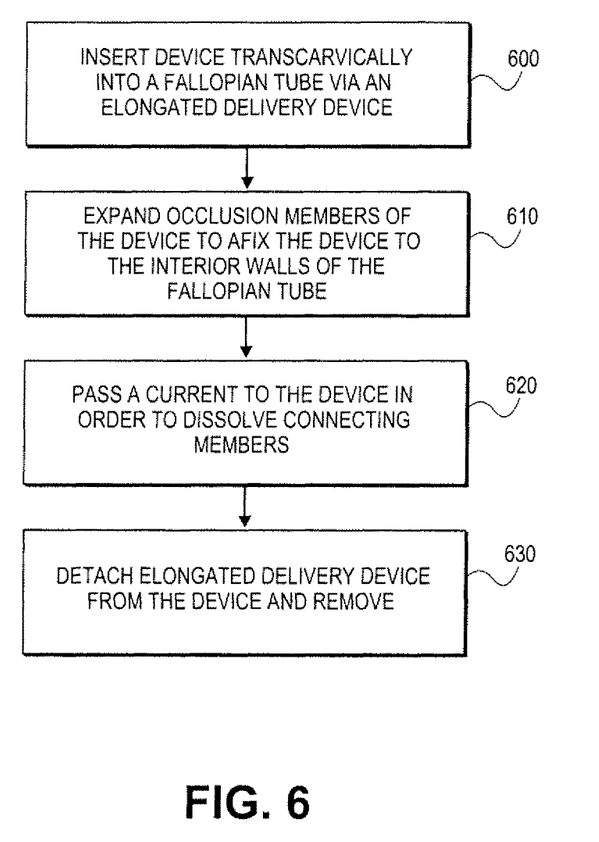
FIG. 6 shows a flow chart of a method to deliver a device in to a fallopian tube.

FIG. 6 shows one embodiment of the invention; a method is shown to deliver the invention described herein. In operation 600 the device is transcervically inserted into a fallopian tube using an elongated delivery device. The elongated delivery device may be inserted into the working channel of a hysteroscope or alternatively positioned using a guide wire or inserted alone and guided by way of fluoroscopy. The elongated delivery device may enclose the device and push the device out to position the device for delivery, or the device may be exposed on the distal portion of the elongated delivery device.

In operation 610 the occlusion members of the device are expanded. The occlusion members may be expanded by releasing potential energy stored in the occlusion device. For example the occlusion members may be physically bound by the elongated delivery device, and immediately expanded by removal from the elongated delivery device. The occlusion members may also be expanded by physically deforming the occlusion members, for example by balloon expansion. The occlusion members may also be a shape-memory material and expanded by exposing the occlusion members to heat or electrical energy delivered by the elongated delivery device.

In operation 620 the occlusion members are separated from each other. In one embodiment, a current is passed by the elongated delivery device to dissolve at least a portion of connecting members which couple the occlusion members to one another. Alternatively the connecting members may be constructed from a rapidly dissolving biodegradable polymer which would dissolve in a short period of time (e.g. hours) before expulsion forces can effectively expel the device.

In operation 630 the elongated delivery device is detached from the device and the removed from the patient. Alternatively the elongated delivery device may include a second device which is used to treat the other fallopian tube.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. A medical device for occluding a fallopian tube, the medical device comprising:
   an elongated member including an outer surface and a circumferential indentation within the outer surface;
   an expandable occlusion member having an unexpanded state and an expanded state and including a radially expandable portion having a diameter and being radially expanded in the expanded state, the diameter being smaller in the unexpanded state than in the expanded state, wherein in the unexpanded state the radially expandable portion is coupled within the elongated circumferential indentation and the diameter is even with the outer surface of the elongated member; and
   a fiber directly coupling the radially expandable portion to the circumferential indentation such that the elongated member remains within the expandable occlusion member in both the unexpanded state and the expanded state.

2. The medical device of claim 1 additionally comprising a plurality of circumferential indentations within the outer surface of the elongated member, a plurality of expandable occlusion members, and a plurality of fibers, each expandable occlusion member having an unexpanded state and an expanded state and including a radially expandable portion having a diameter and being radially expanded in the expanded state, each radially expandable portion respectively coupled to a respective elongated circumferential indentation by a respective fiber, wherein each diameter of the plurality of radially expandable portions is even with the outer surface of the elongated member in the unexpanded state, and wherein the elongated member remains within the plurality of expandable occlusion members in both the unexpanded state and the expanded state.

3. The medical device of claim 2 wherein the plurality of fibers are flexible.

4. The medical device of claim 3 wherein the elongated member floats within the plurality of expandable occlusion members when the plurality of expandable occlusion members are expanded such that the elongated member does not transfer force between individual expandable occlusion members.

5. The medical device of claim 2 wherein the elongated member is constructed from a metal alloy.

6. The medical device of claim 5 wherein the plurality of expandable occlusion members are constructed from a biodegradable polymer.

7. The medical device of claim 2 additionally comprising heating elements for heating the plurality of radially expandable portions coupled to the plurality of circumferential indentations.

8. The medical device of claim 2 wherein the plurality of expandable occlusion members comprise cylindrical coils.

9. The medical device of claim 2 wherein the plurality of expandable occlusion members comprise a mesh structure.

10. The medical device of claim 2 wherein the plurality of expandable occlusion members comprise spider assemblies.

11. The medical device of claim 1 wherein the elongated member is removably coupled to an elongated delivery device.

12. The medical device of claim 11 wherein the elongated member is removably coupled to an elongated delivery device with a joint selected from the group consisting of an interference joint, a threaded joint, and an electrolytically dissolvable joint.

13. The medical device of claim 1 wherein the expandable occlusion member is detachably coupled to the elongated member.

14. The medical device of claim 13 wherein the elongated member is constructed from a biodegradable polymer.

15. The medical device of claim 1 wherein a distal end of the elongated member is rounded.

16. The medical device of claim 15 wherein a distal portion of the medical device is exposed outside a distal end of an elongated delivery device.

17. The medical device of claim 1 wherein the expandable occlusion member is constructed from a biodegradable polymer.

* * * * *